(12) United States Patent
Castillo

(10) Patent No.: US 10,137,027 B2
(45) Date of Patent: Nov. 27, 2018

(54) NASAL APPLIQUE AND RELATED APPLICATOR FOR APPLYING APPLIQUE TO A NOSE OF A WEARER

(71) Applicant: James D. Castillo, Los Alamos, CA (US)

(72) Inventor: James D. Castillo, Los Alamos, CA (US)

(*) Notice: Subject to any disclaimer, the term of this patent is extended or adjusted under 35 U.S.C. 154(b) by 74 days.

(21) Appl. No.: 14/979,009

(22) Filed: Dec. 22, 2015

(65) Prior Publication Data

US 2016/0106567 A1 Apr. 21, 2016

Related U.S. Application Data

(63) Continuation-in-part of application No. 14/799,192, filed on Jul. 14, 2015, which is a continuation-in-part of application No. 14/622,448, filed on Feb. 13, 2015, which is a continuation-in-part of application No. 14/502,348, filed on Sep. 30, 2014.

(60) Provisional application No. 61/918,826, filed on Dec. 20, 2013, provisional application No. 61/937,018, filed on Feb. 7, 2014.

(51) Int. Cl.
A61F 5/08 (2006.01)

(52) U.S. Cl.
CPC ...................... A61F 5/08 (2013.01)

(58) Field of Classification Search
CPC .. A61F 5/08; A61F 5/56; A61M 29/00; A61B 17/24
See application file for complete search history.

(56) References Cited

U.S. PATENT DOCUMENTS 1,714,822 A * 5/1929 Segal .................... A61B 17/30
294/99.2
3,835,848 A 9/1974 Berner
(Continued)

FOREIGN PATENT DOCUMENTS

CN 1389185 1/2003
JP H10192412 7/1998
(Continued)

OTHER PUBLICATIONS

International Search Report and Written Opinion of International Application No. PCT/US15/67530, dated May 16, 2016, 11 pages.
(Continued)

Primary Examiner — Ashley Fishback
(74) Attorney, Agent, or Firm — Stetina Brunda Garred and Brucker

(57) ABSTRACT

A nasal applique and corresponding applicator for placing the applique on the nose of a user. The applique includes a flexible body including a first surface and an opposing second surface with at least one perforation extending from the first surface to the second surface. The first surface includes an adhesive disposed thereon to enable the first surface to be selectively attachable to the nose of the wearer. A metallic element is coupled to the flexible body and is configured to interact with the magnet when the magnet is positioned adjacent the nose of the wearer and the flexible body is attached to the nose of the wearer. The interaction between the metallic element and the magnet imparts a dilating force on the nose of the wearer, which causes the nose of the wearer to dilate.

19 Claims, 7 Drawing Sheets

(56) References Cited

U.S. PATENT DOCUMENTS

| | | |
|---|---|---|
| 4,835,506 A | 5/1989 | Leupold |
| 4,886,349 A | 12/1989 | Willis |
| 5,533,503 A | 7/1996 | Doubek et al. |
| 5,566,503 A | 7/1996 | Doubek et al. |
| 5,719,655 A | 2/1998 | Peschel et al. |
| 5,913,873 A | 6/1999 | Blach et al. |
| 5,957,126 A | 9/1999 | Neeser |
| 6,006,746 A | 12/1999 | Karell |
| 6,033,422 A | 3/2000 | Blach et al. |
| 6,352,548 B1 | 3/2002 | Blach et al. |
| 6,533,412 B1 | 3/2003 | Wang et al. |
| 6,540,349 B1 | 4/2003 | Liesegang |
| 6,648,471 B1 | 11/2003 | Dalrymple et al. |
| 6,676,681 B1 | 1/2004 | Blach et al. |
| 6,823,864 B2 | 11/2004 | Blach et al. |
| 7,091,634 B2 | 8/2006 | Yi et al. |
| 7,118,210 B2 | 10/2006 | Landers |
| 7,793,661 B2 | 9/2010 | Macken |
| D639,762 S | 6/2011 | Brogden et al. |
| D644,324 S | 8/2011 | Brunner et al. |
| D644,325 S | 8/2011 | Brunner et al. |
| 8,042,542 B2 | 10/2011 | Ging et al. |
| 8,292,427 B2 | 10/2012 | Zelazowski |
| 8,459,254 B1 | 6/2013 | Jassir et al. |
| D696,400 S | 12/2013 | Brogden et al. |
| D701,957 S | 4/2014 | Brunner et al. |
| D703,318 S | 4/2014 | Brunner et al. |
| 2002/0029408 A1 | 3/2002 | Lindahl |
| 2003/0000521 A1 | 1/2003 | Beaudry |
| 2007/0105824 A1 | 5/2007 | Erickson-Miller et al. |
| 2007/0252946 A1 | 11/2007 | Welchel |
| 2008/0097517 A1 | 4/2008 | Holmes et al. |
| 2008/0119885 A1 | 5/2008 | Yazdi |
| 2009/0183734 A1 | 7/2009 | Kwok et al. |
| 2009/0188023 A1 | 7/2009 | Hsu |
| 2010/0309425 A1 | 12/2010 | Zelazowski |
| 2011/0000483 A1 | 1/2011 | Matthias et al. |
| 2012/0024639 A1 | 2/2012 | Castro |
| 2012/0036607 A1 | 2/2012 | Beliveau |
| 2012/0172923 A1 | 7/2012 | Fenton et al. |
| 2014/0296904 A1 | 10/2014 | Andre |
| 2014/0375946 A1 | 12/2014 | Rochford et al. |
| 2015/0001014 A1 | 1/2015 | Noborio et al. |
| 2015/0173933 A1 | 6/2015 | Castillo |
| 2015/0173934 A1 | 6/2015 | Castillo |

FOREIGN PATENT DOCUMENTS

| | | |
|---|---|---|
| JP | 2009-535079 | 10/2009 |
| KR | 200404740 | 12/2005 |
| WO | WO2002/003125 | 1/2002 |

OTHER PUBLICATIONS

International Search Report and Written Opinion of International Application No. PCT/US2016/022637, dated Jun. 9, 2016, 10 pages.

International Search Report and Written Opinion for International Application No. PCT/US14/69817, dated Mar. 11, 2015, 11 pages.

First Office Action of CN Application 201480075735.9, dated May 2, 2017, 9 pages.

Summary of First Office Action of CN Application 2014800757359, dated May 2, 2017, 5 pages.

Australian Government IP Australia, Examination report No. 1 for standard patent application, dated Oct. 24, 2017, 5 pages.

Office Action for corresponding Japanese Patent Application No. 2016-560622 with English translation, dated Nov. 1, 2017, 5 pages.

International Search Report and Written Opinion for International Application No. PCT/US 17/45688, dated Oct. 31, 2017, 11 pages.

European Patent Office, extended European search report for Application No. EP 14871764, dated Jul. 7, 2017, 10 pages.

Patent Cooperation Treaty, International Preliminary Report on Patentability for Application No. PCT/US16/22637, dated Aug. 3, 2017, 9 pages.

* cited by examiner

NASAL APPLIQUE AND RELATED APPLICATOR FOR APPLYING APPLIQUE TO A NOSE OF A WEARER

CROSS-REFERENCE TO RELATED APPLICATIONS

This application is a continuation-in-part of U.S. patent application Ser. No. 14/799,192, filed Jul. 14, 2015, which is a continuation-in-part of U.S. patent application Ser. No. 14/622,448, filed Feb. 13, 2015 and published as United States Patent Application Publication No. 2015/0173934, which is a continuation-in-part of U.S. patent application Ser. No. 14/502,348, filed Sep. 30, 2014 and published as United States Patent Application Publication No. 2015/0173933, which claims the benefit of U.S. Provisional Application No. 61/918,826, filed Dec. 20, 2013, and U.S. Provisional Application No. 61/937,018, filed Feb. 7, 2014, the contents of each of the foregoing applications being expressly incorporated herein by reference.

STATEMENT RE: FEDERALLY SPONSORED RESEARCH/DEVELOPMENT

Not Applicable

BACKGROUND

1. Technical Field

The present invention relates generally to components for breathing enhancement, and more specifically to a nasal applique wearable on a user's nose for use with a breathing enhancement system and a related device for easily and correctly placing the appliques on the user's nose.

2. Description of the Related Art

It is readily understood that breathing is important when playing sports or taking part in physical competition due to the increased demand for oxygen by the body. Breathing may be achieved by drawing air into the body through an individual's nostrils and/or through the individual's mouth. However, in some instances, it is preferable to breathe almost exclusively through the nostrils, as there may be a downside to breathing through one's mouth. Along these lines, breathing through the mouth may lead to rapid water loss and heat loss, both of which increase the likelihood of exercise-induced asthma.

It is also understood that eyewear is commonly used when participating in many sports and activities. Such eyewear may include protective eyewear, or vision-enhancing (e.g., prescription) eyewear. For instance, goggles are readily worn by many athletes participating in snowboarding, skiing, motocross, automotive racing, basketball, baseball, hockey, etc. Goggles are typically configured such that a portion of the goggle frame extends over the wearer's nose, and thus, goggles may impact one's ability to breathe through the wearer's nasal passage. Along these lines, many goggles are fitted with a foam liner which interfaces with the wearer's face to create a barrier or seal which prevents snow, rain, dirt or other debris from entering the goggles and creating a potential irritant in the wearer's eye. In order to create an effective seal or barrier around the goggles, the goggles are compressed against the wearer's face, typically through the use of an elastic band which is worn around the head. The compression of the foam liner against the wearer tends to compress the nasal passages of the wearer, which further inhibits the ability of the wearer to breathe through the nose.

Accordingly, there is a need in the art for a device which can be used with a goggle or other eyewear for enhancing the wearer's ability to breathe through the wearer's nasal passage. Furthermore, in view of the unique anatomy associated with the nose, there is a need to ensure such breathing enhancement device is properly applied to the user's nose. Various aspects of the present invention address this particular need, as will be discussed in more detail below.

BRIEF SUMMARY

In accordance with one embodiment of the present disclosure, there is provided a disposable apparatus (e.g., an applique) attachable to the nose of a user, the apparatus being adapted for use with a magnet to impart a dilating force on the user's nose to open the nasal passages to increase the efficiency of the user's breathing.

According to one particular embodiment, the disposable apparatus includes a flexible body including a first surface and an opposing second surface with at least one perforation extending from the first surface to the second surface. The first surface includes an adhesive disposed thereon to enable the first surface to be selectively attachable to the nose of the wearer. A metallic element is coupled to the flexible body and is configured to interact with the magnet when the magnet is positioned adjacent the nose of the wearer and the flexible body is attached to the nose of the wearer. The interaction between the metallic element and the magnet imparts a dilating force on the nose of the wearer, which causes the nose of the wearer to dilate.

The flexible body may include a plurality of perforations extending from the first surface to the second surface. The plurality of perforations may be spaced radially outward from the metallic element. The plurality of perforations may be spaced from an outer periphery of the flexible body. Each of the plurality of perforations may be generally linear and extends in a radially outward direction relative to the metallic element. The plurality of perforations may include a first set of perforations extending in a first axial direction and a second set of perforations extending in a second axial direction generally perpendicular to the first axial direction.

At least a portion of the flexible body may extend radially outward beyond the metallic element to define a flexible peripheral portion. The flexible body may include a first layer and a second layer attached to the first layer, with the metallic element being captured between the first layer and the second layer. A peel-away layer may be coupled to the flexible body and covering the adhesive disposed on the first surface.

The flexible body may define a flexible body plane, and the metallic element may have a generally planar first surface substantially parallel to the flexible body plane, and an arcuate second surface coupled to the first surface of the metallic element.

According to yet another embodiment, there is provided an applicator for placing a pair of nasal appliques on opposing lateral regions of a nose of a user. The applicator includes a base and a nose rest coupled to the base and adapted to rest adjacent the nose of the user. A pair of stop members are coupled to the base and are arranged in generally opposed relation to each other. A pair of applicating elements are also coupled to the base, with each applicating element being engageable with a respective one of the pair of nasal appliques. Each applicating element is selectively transitional between a first position and a second position. When each applicating element is in its first position, the applicating element is positioned adjacent the respective one of the pair of stop members, and when each applicating element is in its second position, the applicating element is moved away from the respective one of the pair of stop members for placing the respective one of the pair of nasal appliques on the nose of the user.

The nose rest may be translatably coupled to the base. The applicator may additionally include an adjuster coupled to the base and the nose rest, with the adjuster being configured to enable selective translational adjustment of the nose rest relative to the base.

Each applicating element may include a magnet adapted to impart a magnetic force on a corresponding metallic element included in the respective one of the pair of nasal appliques. Each applicating element may also include an arm coupled to the base, and a pad coupled to the arm. The pad may be pivotally coupled to the arm. The arm and the base may be configured to allow the arm to flex relative to the base as the applicating element transitions between the first and second positions. The arm may be integrally coupled with the base.

Each stop member may include a primary wall and a peripheral wall extending from the primary wall, with the primary wall and peripheral wall collectively defining a cavity adapted to receive at least a portion of a respective one of the pair of applicating elements in the first position. The primary wall may be disposed about an opening through which the respective one of the pair of applicating elements extends.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

Figure 1:
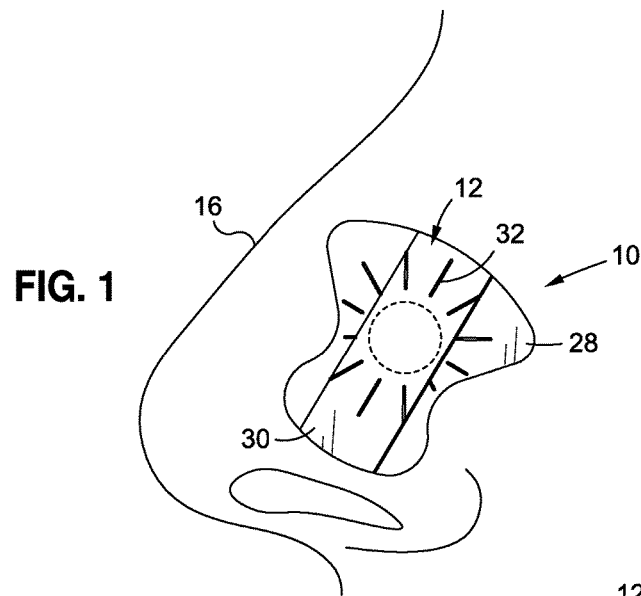
FIG. 1 is a top view of an embodiment of a nasal applique positioned on a lateral region of a wearer's nose, the nasal applique having perforations arranged in a starburst pattern.

The detailed description set forth below in connection with the appended drawings is intended as a description of certain embodiments of a nasal applique for a breathing system and a related device for applying the applique to the user and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

According to one embodiment, there is provided a disposable apparatus, e.g., a nasal applique 10, specifically configured and adapted for use in a breathing enhancement system. As will be described in more detail below, one embodiment of the breathing enhancement system utilizes magnetic forces between a remotely located magnet and a metallic element included in the applique 10 to impart a dilating force on the user's nose to open the user's nasal passage. An exemplary breathing enhancement system with which the nasal applique 10 may be used is disclosed in United States Patent Application Publication Nos. 2015/0173934 and 2015/0173933, the contents of which are expressly incorporated herein by reference.

The nasal applique 10 generally includes a flexible body 12 and the metallic element 14 coupled to the flexible body 12. The flexible body 12 is configured to be attached to a lateral region of the user's nose 16, with the flexible body 12 being capable of bending/flexing to conform to the unique anatomy of the user's nose 16. According to one embodiment, the flexible body 12 includes a first surface 18 and an opposing second surface 20. The first surface 18 includes an adhesive disposed thereon to enable the first surface 18 to be selectively attachable to the nose 16 of the wearer. A peel-away layer 22 may be coupled to the flexible body 12 and cover the adhesive disposed on the first surface 18 to preserve the adhesive until the applique 10 is to be used.

Figure 2:
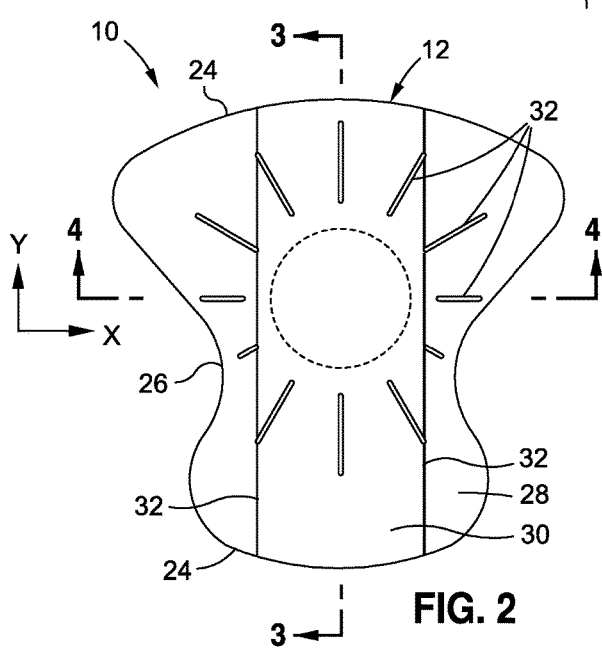
FIG. 2 is a top view of the nasal applique depicted in FIG. 1.
Figure 3:
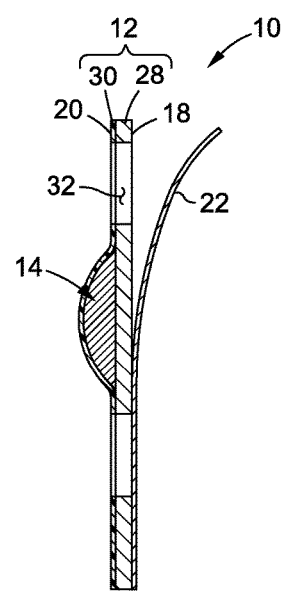
FIG. 3 is a side cross sectional view of the applique depicted in FIG. 2 taken along line 3-3.
Figure 4:
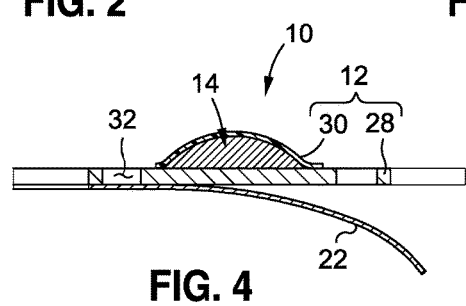
FIG. 4 is an end cross sectional view of the applique depicted in FIG. 2 taken along line 4-4.

According to one embodiment, and when viewed in from the perspective depicted in FIGS. 1 and 2, the flexible body 12 defines an outer periphery that is generally of the shape of an hour-glass or butterfly. In this respect, the outer periphery includes a pair of enlarged end portions 24 separated by a narrow middle portion 26 having a pair of opposed concave edges. The exemplary embodiment includes end portions 24 which are not identical; rather, one end portion is slightly larger than the other end portion. However, it is understood that in other embodiments, the end portions may be identical. The generally hour-glass configuration of the outer periphery may enable the flexible body 12 to more easily conform to the unique anatomy of the user's nose 16. For instance, one end portion of the flexible body 12 may extend onto the "ala of the nose," e.g., the rounded eminence extending around the nostril, the middle portion of the flexible body 12 may extend over the alar crease, and the remaining end portion of the flexible body 12 may extend on an adjacent region of the nose 16.

According to one embodiment, the flexible body 12 is a composite structure including a first layer 28 and a second layer 30 attached to the first layer 28. Of course, additional layers may be added to the flexible body 12 without departing from the spirit and scope of the present disclosure. The metallic element 14 is captured between the first layer 28 and the second layer 30, with the metallic element 14 being configured to interact with a magnet when the magnet is remotely positioned adjacent the nose 16 of the wearer and the flexible body 12 is attached to the nose 16 of the wearer. The metallic element 14 is positioned such that at least a portion of the flexible body 12 extends radially outward beyond the metallic element to define a flexible peripheral portion. The interaction between the metallic element 14 and the magnet imparts a dilating force on the nose 16 of the wearer, which causes the nose 16 of the wearer to dilate. In this respect, the applique 10 is specifically configured and adapted to selectively transition between an "ON" state and an "OFF" state, depending on the location of the external magnet. If the magnet is in close proximity to the applique 10 residing on the user's nose 16, the metallic element 14 is drawn towards the magnet and thus, the applique 10 imparts the dilating force on the nose 16. In contrast, if the magnet is not in close proximity to the user's nose 16, the metallic element is not drawn towards the magnet, and thus, no dilating force is imparted on the nose 16 by the applique 10. The ability to selectively transition between ON and OFF states without requiring removal of the applique 10 is a significant benefit, as it allows a user to place the applique 10 on at the beginning of an athletic event, and keep the applique 10 on the nose 16 throughout the duration of the athletic event, while allowing the user to selectively transition the applique 10 between the ON and OFF states. Such ability is a significant departure from existing nasal "strips" which use a spring-biased metal strip to open a user's nasal passageway. The existing nasal strips continuously apply a dilating force on the user's nose the entire time the nasal strip is coupled to the nose. In this regard, the conventional nasal strip does not include the ability to seamlessly transition between ON and OFF states based on the proximity of a magnet.

In one implementation, the second layer 30 is smaller than the first layer 28, with the second layer 30 being only large enough to extend between opposing edges of the first layer 28 and cover the metallic element 14, which may protect the user from the edges of the metallic element 14. In this respect, the second layer 30 defines a pair of opposed edges 32 defining a second layer width therebetween, wherein the second layer width is slightly larger than the diameter of the metallic element 14 so as to effectively capture the metallic element 14 between the first and second layers 28, 30. Thus, the second layer 30 need not have an outer periphery that is coextensive with the first layer 28. Since the second layer 30 may only partially cover the first layer 28, the second surface 20 may be collectively defined by both the first layer 28 and the second layer 30. In particular, the entirety of the second layer 30 may define a portion of the second surface 20, while only those exposed portions of the first layer 28 may define the second surface 20. In this respect, the second surface 20 may be the exposed surface collectively defined by the first and second layers 28, 30.

In the embodiment depicted in FIGS. 1-4, the second layer 30 extends relative to the first layer 28 in a longitudinal direction, e.g., the second layer 30 extending from one enlarged end portion 24 to the other enlarged end portion 24. In this respect, the second layer 30 is spaced from the opposed concave edges of the first layer 28.

According to one implementation, the first layer 28 has adhesive on each of the opposing surfaces thereof. In particular, the first layer 28 includes adhesive on the surface which is attachable to the user's nose, as well as the surface which interfaces with the metallic element 14, as well as the second layer 30 so as to mitigate inadvertent separation between the first and second layers 28, 30. As to the second layer 30, it is also preferred that the surface which interfaces with the metallic element 14 and the first layer 28 also have adhesive.

Figure 5:
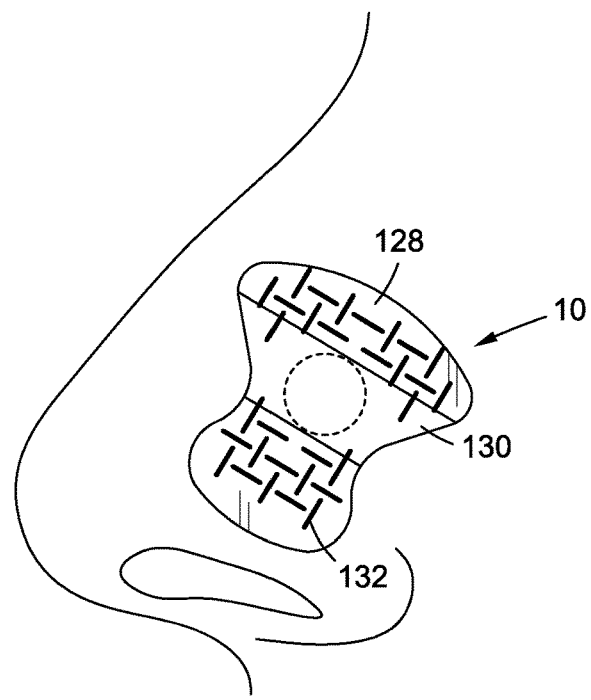
FIG. 5 is a top view of another embodiment of a nasal applique positioned on a lateral region of a wearer's nose, the nasal applique having perforations arranged in a cross-hatch pattern.
Figure 6:
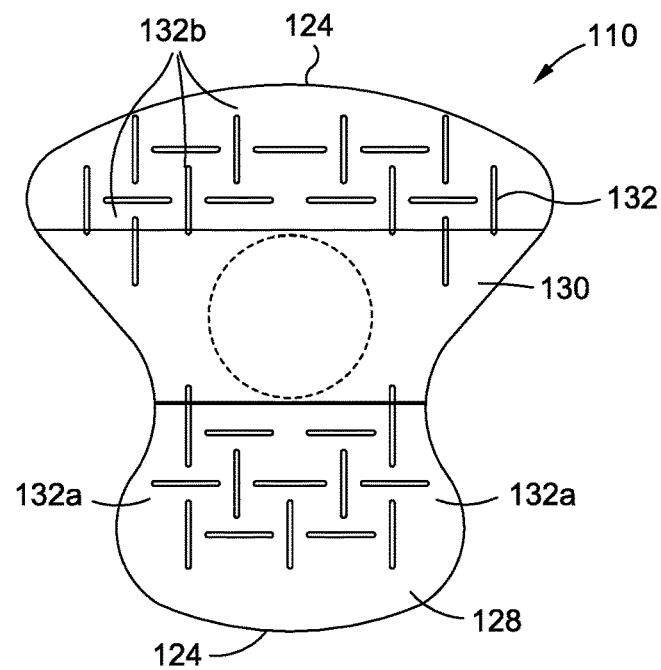
FIG. 6 is a top view of the nasal applique depicted in FIG. 5.

Another embodiment of an applique 110 is shown in FIGS. 5-6, with the applique 110 being similar to the applique 10 discussed above. In view of the commonalities between the applique 10 shown in FIGS. 1-4 and the applique 110 shown in FIGS. 5-6, the discussion of applique 110 will focus on the unique attributes thereof relative to applique 10. One unique feature of the applique 110 is the orientation of the second layer. More specifically, the applique 110 includes a first layer 128 and a second layer 130, wherein the second layer 130 extends in a direction generally perpendicular to the direction of the second layer 30 shown in FIGS. 1-4. In other words, the second layer 130 in FIGS. 5-6 extends between the opposed concave edges along the middle portion of the applique 110, and is spaced from the enlarged end portions 124. One particular advantage to orienting the second layer 130 as shown in FIGS. 5-6 is that less material may be required for the second layer 130, since it extends along the narrow, latitudinal section of the applique 10, rather than along the enlarged, longitudinal section thereof.

Referring back to FIGS. 1-4, and according to one embodiment, the flexible body 12 includes at least one perforation 32 extending from the first surface 18 to the second surface 20. In this regard, depending on the location of the perforation 32, the perforation 32 may extend through only the first layer 28, or through both the first layer 28 and the second layer 30. The perforations 32 are adapted to ventilate the user's skin residing under the applique 10 to prevent sweat from building up under the applique 10. Along these lines, a buildup of sweat between the applique 10 and the user's skin could diminish the ability of the adhesive to effectively secure the applique 10 to the user's nose 16. Thus, by incorporating the perforation(s) 32, the sweat can evaporate or flow away from the user's skin to more effectively maintain adhesion between the applique 10 and the user's nose 16.

According to one embodiment, the applique 10 includes a plurality of perforations 32 which are spaced radially outward from the metallic element 14. In this respect, the perforations 32 may be located in that portion of the flexible body 12 extending between the outer periphery of the metallic element 14 and the outer periphery of the flexible body 12. In certain embodiments, the perforations 32 may be spaced from outer periphery of the flexible body 12, while in other embodiments, one or more perforations 32 may extend all the way to the outer periphery of the flexible body 12.

Referring now specifically to FIGS. 1-4, the perforations form a "starburst" pattern, with each perforation 32 being generally linear and extending in a radially outward direction relative to the metallic element 14. The exemplary starburst pattern includes twelve perforations 32 spaced equally about the metallic element 14. It is understood that the size of the perforations 32 may vary, e.g., some perforations 32 may be shorter in length than others, and that the number of perforations 32 may also vary. In this respect, there may be as few as one perforation 32, while in other embodiments, there may be more than twelve perforations 32 without departing from the spirit and scope of the present disclosure.

Referring now back to FIGS. 5-6, the applique 110 shown therein includes a plurality of perforations 132 in a different arrangement from that shown in FIGS. 1-4. In particular, the applique 110 includes a plurality of perforations 132 arranged in a cross-hatch pattern. In particular, the plurality of perforations 132 includes a first set of perforations 132a extending in a first axial direction and a second set of perforations 132b extending in a second axial direction generally perpendicular to the first axial direction.

Although the foregoing shows appliques 10, 110 having linear perforations arranged in a starburst pattern and a cross-hatch pattern, it is understood that that the perforations may take on other shapes and/or configurations. In this respect, the perforations are not limited to linear perforations; rather, the perforations may be circular, triangular, quadrangular, curvilinear, etc. Furthermore, the perforations may be arranged in any pattern or arrangement known by those skilled in the art.

Referring now to the particulars of the metallic element 14, the exemplary embodiment of the metallic element 14 includes a convex surface defining a "domed" configuration to enhance magnetic engagement with the remotely located magnet. In this regard, flat-to-flat attachment between the magnet and the metallic element 14 may create uncomfortable torque on the user's nose. Thus, by creating a domed engagement surface on the metallic element, such uncomfortable torque may be avoided. Furthermore, the convex surface defines an engagement surface which the magnet may engage with and move along during engagement between the applique 10 and the magnet. In particular, the magnet may move along at least two axes, particularly, the X and Y axes (as shown in FIG. 2) relative to the metallic element 14 while the metallic element 14 remains engaged with the magnet.

The domed or arcuate surface may be positioned opposite a generally planar surface of the flexible body 12, such as substantially parallel to a flexible body plane defined by the flexible body 12. It is understood that the outer periphery of the metallic element 14 may be any shape, including circular, oval, quadrangular, etc. The advantages of the convex engagement between the metallic element 14 and the corresponding magnet may also be effectuated through the use of an arcuate or dome shaped magnet. In this respect, the metallic element 14 and/or the magnet may have an arcuate or rounded surface.

Although the foregoing refers to the specifics of the applique, the following discussion, in conjunction with FIGS. 7-10, focuses on an applicator 200 for easily placing a pair of nasal appliques 10 on opposing lateral regions of the nose 16 of a user. According to one embodiment, the applicator 200 includes a base 202 and a nose rest 204 translatably coupled to the base 202. The nose rest 204 includes a translation body 206 and a nose pad 208 coupled to the translation body 206. The nose pad 208 may be specifically configured and adapted to engage with the user's nose 16. Along these lines, the nose pad 208 may include a curved or arcuate engagement surface, and a cushion 210 to provide a cushioned surface against the user's nose 16 during use of the applicator 200. The cushion 210 may include a face which contacts the user's nose during use, wherein the face includes an upper portion and a lower portion which is angled relative to the upper portion. In particular, the upper and lower portions may taper outwardly toward their intersection.

An adjuster 212 is coupled to the base 202 and the translation body 206, with the adjuster 212 being configured to enable selective translational adjustment of the translation body 206 relative to the base 202. Adjustment of the translation body 206 allows control over the depth of the appliques 10 on the user's nose (e.g., the distance of the appliques 10 from the front of the nose). In the exemplary embodiment, the adjuster 212 includes a screw which is received within a cavity formed within the base 202, with the screw being capable of rotating relative to the base 202, although the screw remains relatively stationary in an axial direction relative to the base 202, e.g., the screw may rotate relative to the base 202, although the screw does not translate relative to the base 202. The screw includes a screw head 214 located within a first cavity portion 216 formed in the base 202, with the first cavity portion 216 generally corresponding to the size of the screw head 214 to capture the screw head 214 therein. An externally threaded shaft 218 extends from the head 214 and through a second cavity portion 220 defined by the base 202 and into threaded engagement with the translation body 206. When the screw is rotated in a first rotational direction, the threaded engagement between the shaft 218 and the translation body 206 causes the translation body 206 to translate relative to the base 202 in a first axial direction, and when the screw is rotated in an opposing second rotational direction, the threaded engagement between the shaft 218 and the translation body 206 causes the translation body 206 to translate relative to the base 202 in an opposing second axial direction. According to one embodiment, the translation body 206 fits over the base 202 to slide/translate over the base 202. The translation body 206, base 202, and screw may be adapted to allow the translation body 206 to translate relative to the base 202 between a first position and a second position, wherein the translation body 206 translates away from a distal end 222 of the base 202 as the translation body 206 translates from the first position toward the second position.

It is contemplated that the screw may be adapted to be rotated by the user through the use of a tool, such as an Allen wrench, screwdriver or the like. Alternatively, the screw may be adapted to enable direct manual control by the user, e.g., the user may rotate the screw head with a finger. Furthermore, although the foregoing describes adjustability of the translation body 206 relative to the base 202 via a screw, it is contemplated that any other mechanism known in the art for controlling the position of the translation body 206 relative to the base 202 may also be used without departing from the spirit and scope of the present disclosure.

The applicator 200 further includes a pair of applicating elements 224 (e.g., placement members) and a corresponding pair of stop members 226, with each applicating element 224 being operatively associated with one of the stop members 226. The applicating elements 224 are transitional between first and second positions relative to the stop members 226, with the applicating elements 224 being transitioned from the first position to the second position when applying appliques 10 on the user's nose 16, as will be described in more detail below.

According to one embodiment, each applicating element 224 includes an arm 228 including a fixed end portion 230 coupled to the base 202 and a free end portion 232 extending away from the base 232. The fixed end portion 230 of each arm 228 is coupled to opposed lateral portions of the base 202. According to one embodiment, the arms 228 are integrally coupled with the base 202, although it is understood that the arms 228 and base 202 may be separately formed components. Each arm 228 is of a generally arcuate configuration, with the free end portion 232 being spaced laterally outward relative to the base 202. An applicator plate/pad 234 is coupled to each arm 228, with each applicator pad 234 being adapted to engage with a nasal applique 10 for application on the user's nose 16. In the exemplary embodiment, each applicator pad 234 is coupled to a respective one of the arms 228 via a ball and socket joint 242 to enable pivotal movement of the applicator pad 234 relative to the arm 228. Such pivotal movement may be desirable when pressing the applique 10 onto the nose 16, as the ability of the applicator pad 234 to pivot allows the applicator pad 234 to automatically match the average angle the user's nose 16. As shown, a ball 235 is coupled to the arm 228 and a socket 237 adapted to receive the ball 235 is coupled to the applicator pad 234. However, it is understood that the arrangement of the ball and socket joint may be reversed, with the ball 235 being coupled to the applicator pad 234 and the socket 237 coupled to the arm 228.

Due to the cooperative relationship between the applicator pad 234, the stop members 226, and the nasal applique 10, the configuration of the stop members 226 and applicator pad 234 generally mimics the configuration of the nasal applique 10, and the peripheral configuration of the stop members 226 generally mimics the peripheral configuration of the applicator pad 234 and the nasal applique 10. Therefore, in one embodiment, the applicator pad 234 and stop members 226 may be interchangeable for use with different sizes or shapes of appliques 10.

A magnet 240 is coupled to each applicator pad 234, with the magnet 240 being adapted to impart a magnetic force on a corresponding metallic element 14 included in the nasal appliques 10 for maintaining the nasal appliques 10 in engagement with the applicator pads 234 prior to coupling of the appliques 10 to the user's nose 16. The magnet 240 is received within an opening formed in the applicator pad 234, with the magnet 240 preferably being slightly offset or recessed relative to the surface of the applicator pad 234 which engages with the applique 10. In this respect, the recessed position of the magnet 240 allows the metallic element 14 to be at least partially received within the opening formed within the applicator pad 234 which allows the flexible body 12 of the applique 10 to rest in flush contact with the applicator pad 234. The magnet 240 may be placed in the pad 234 so as to provide a magnetic field but not necessarily make contact with the applique 10.

The arms 228 and applicator pads 234 are arranged in generally opposing relation to each other. In particular, one arm 228 extends from one side of the base 202, while the other arm 228 extends from the other side of the base 202, such that the applicator pads 234 face each other. The opposing surfaces of the pads 234 may be generally planar, or alternatively, the surfaces may define a degree of curvature, and thus, may be arcuate in nature. The arms 228 are adapted to flex relative to the base 202 as the applicating elements 224 transition between the first and second positions. In other words, as the arms 228 move toward each other, the applicating elements 224 transition from the first position toward the second position, and as the arms 228 move away from each other, the applicating elements 224 transition from the second position back toward the first position.

Figure 7:
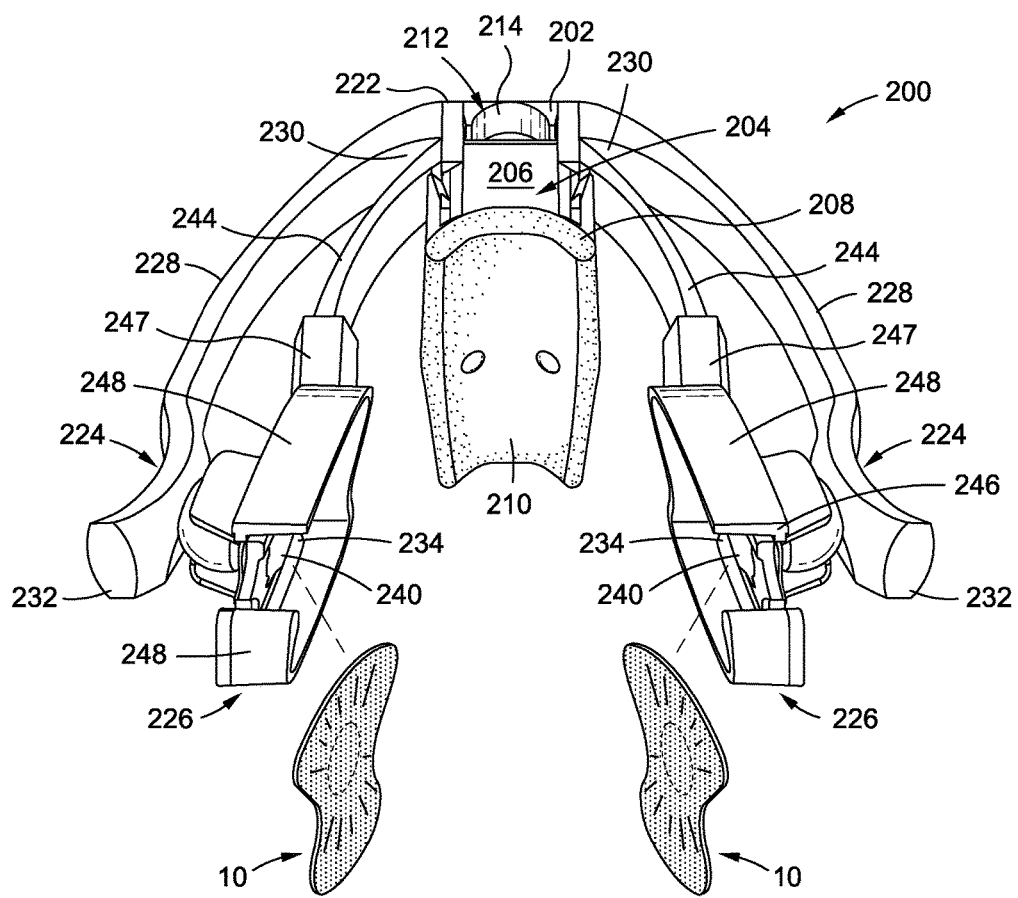
FIG. 7 is an upper perspective view of an applicator and a pair of nasal appliques separated from the applicator.
Figure 7A:
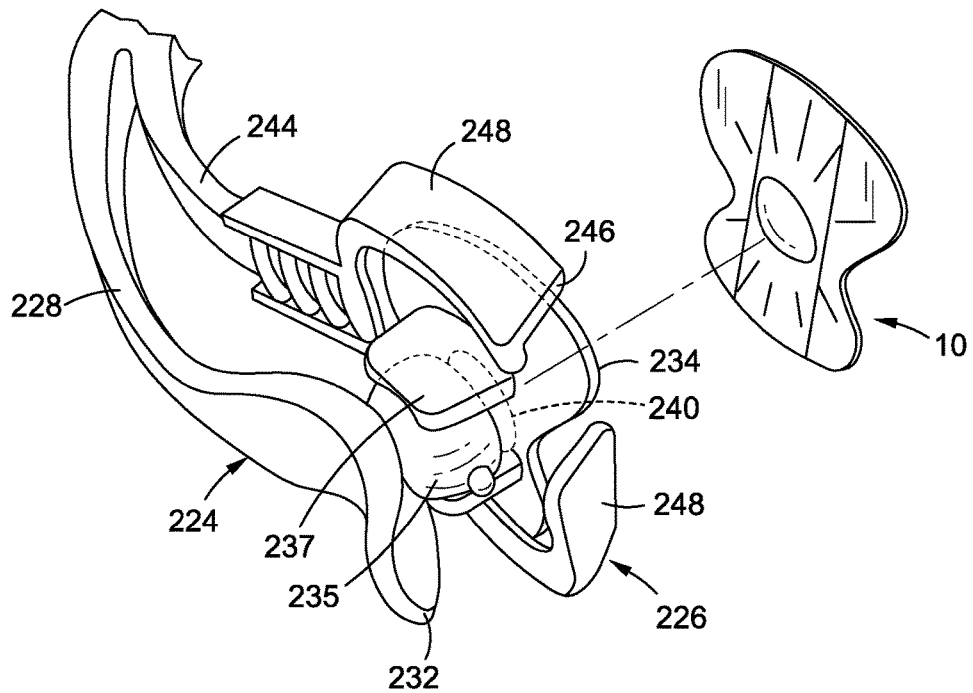
FIG. 7A is an upper perspective view of a ball-and-socket joint connecting an applicating pad to an arm.
Figure 7B:
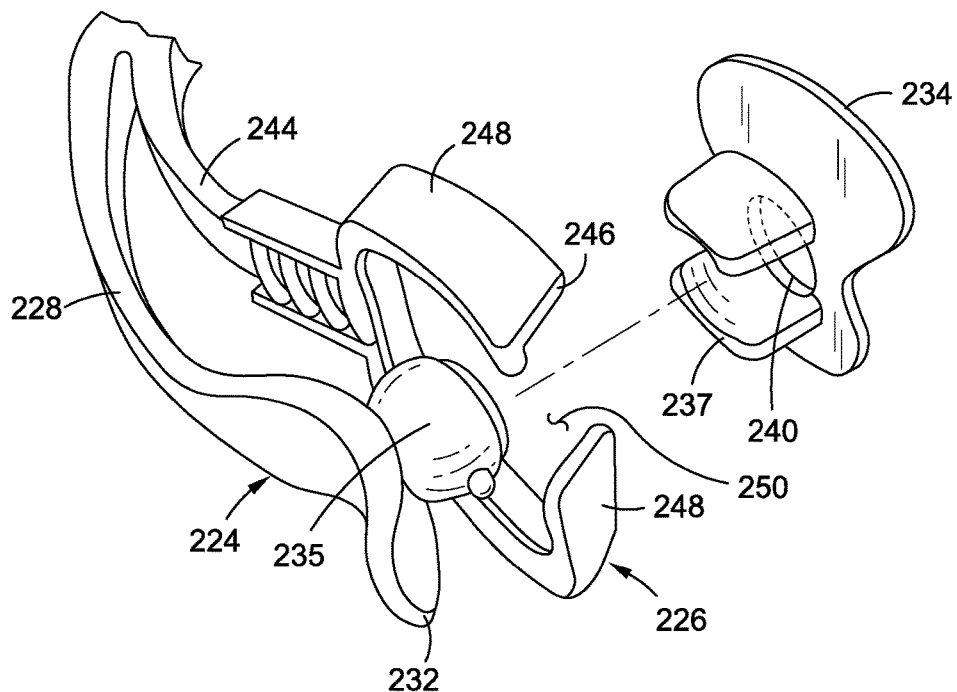
FIG. 7B is an upper perspective view of the ball-and-socket joint depicted in FIG. 7A, with the applicating pad exploded from the arm.
Figure 8:
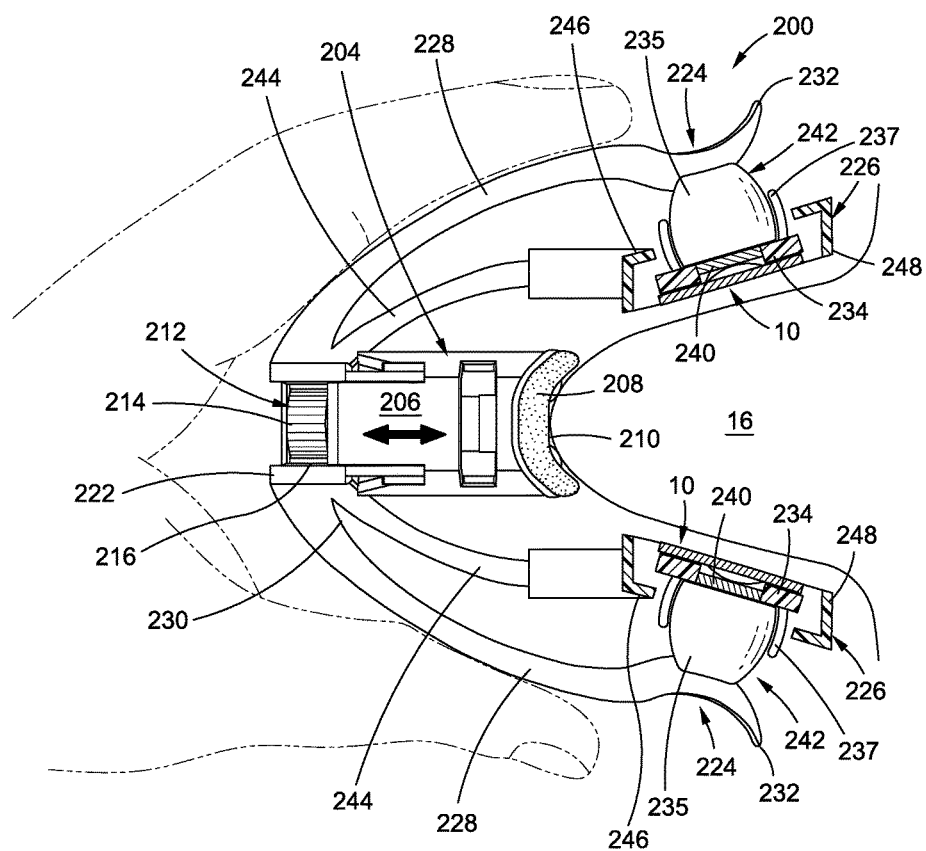
FIG. 8 is a top view of the applicator and nasal appliques coupled to the applicator and ready for application on respective lateral regions of the wearer's nose.
Figure 9:
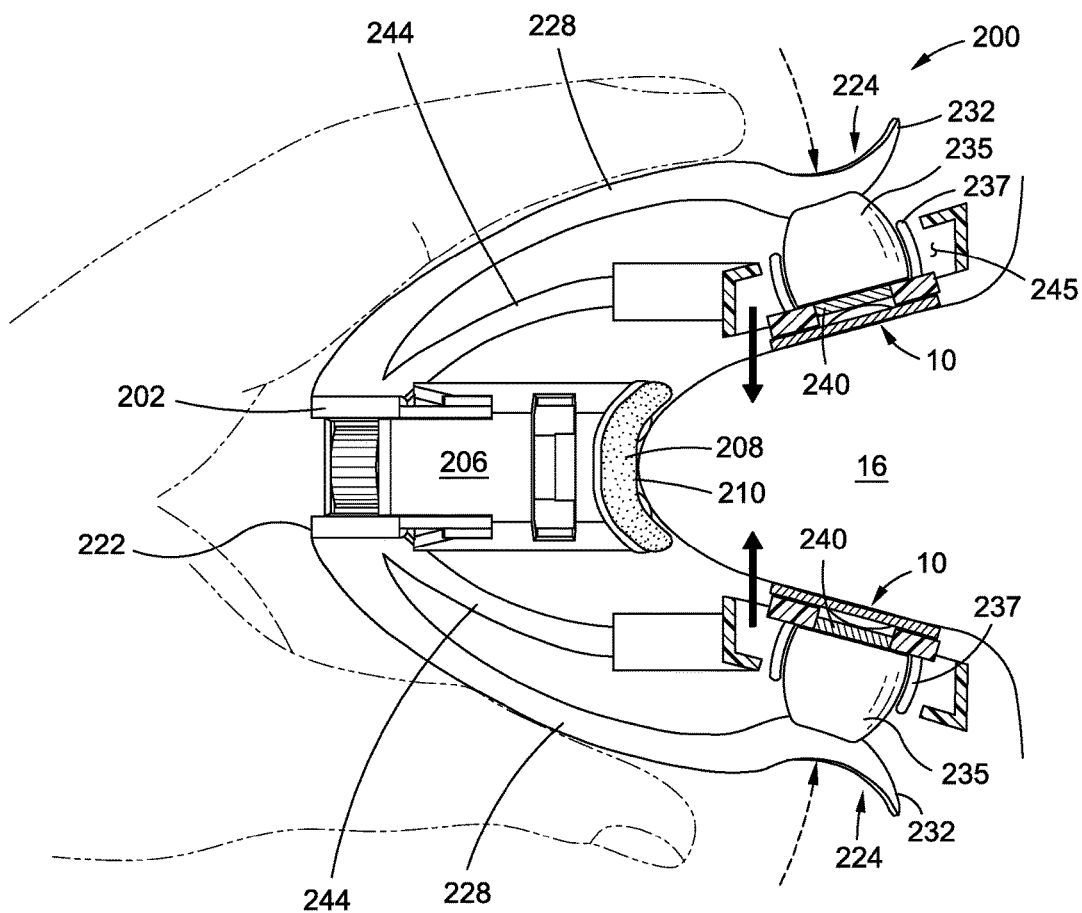
FIG. 9 is a top view of the applicator and nasal appliques, with the appliques being pressed to the respective lateral regions of the wearer's nose.
Figure 10:
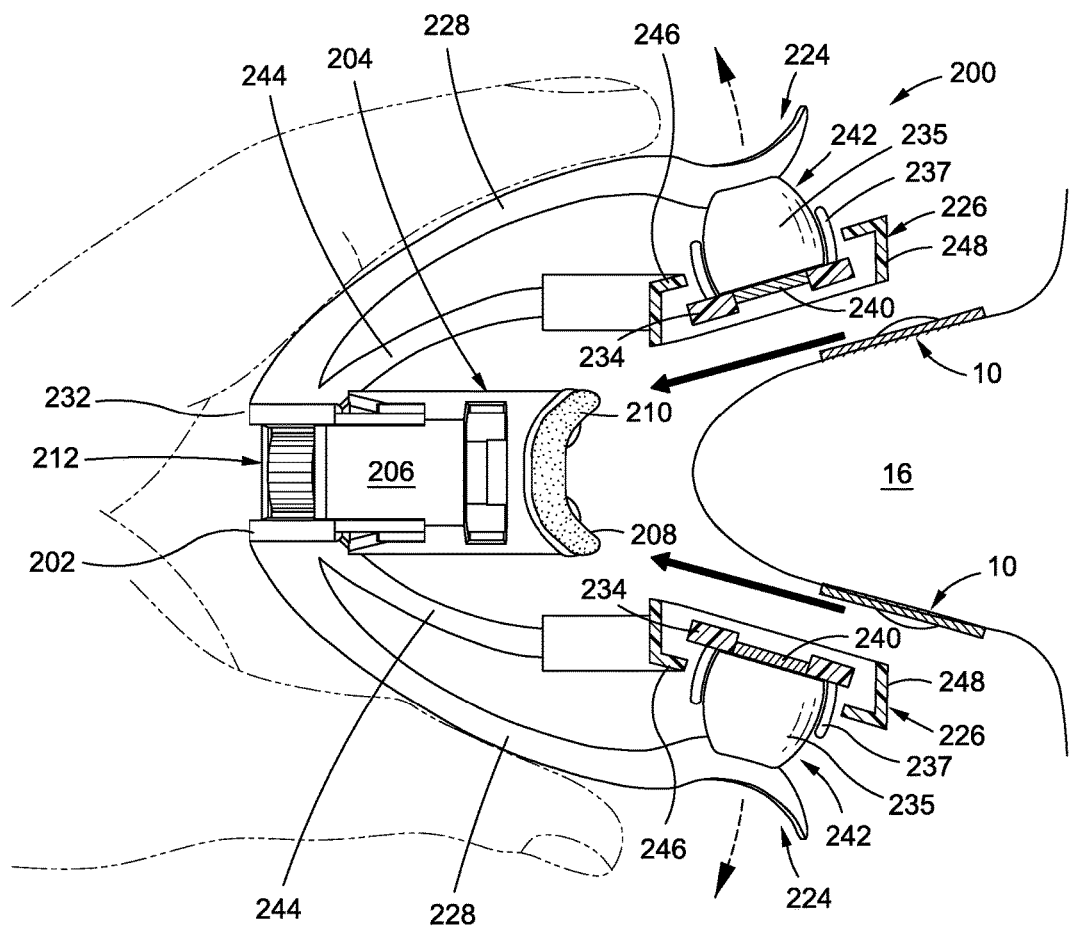
FIG. 10 is a top view of the applicator being retracted from the user's nose subsequent to application of the appliques on the wearer's nose.

The stop members 226 are coupled to the base 202 via extension members 244 and are arranged in generally opposed relation to each other. The stop members 226 may include a sleeve 247 which fits over a portion of the extension member 244 to enable removable engagement between the stop members 226 and the respective extension members 244. According to one embodiment, each stop member 226 includes a primary wall 246 and a peripheral wall 248 extending from the primary wall 246, with the primary wall 246 and peripheral wall 248 collectively defining a cavity 245 adapted to receive at least a portion of a respective applique 10. The primary wall 246 is disposed about, and thus, defines an opening through which a portion of the respective applicating elements 224 may extend. The peripheral wall 248 may include a cutout or gap 250 (see FIG. 7B) formed therein to allow a user to easily access a peel-away layer on an applique 10 magnetically coupled to the applicator pad 234. In particular, a portion of the applique 10 may extend through the gap 250 to allow the user to remove the peel-away layer from the applique 10 prior to pressing the applique 10 on the user's nose.

When each applicating element 224 is in its first position, the applicator pad 234 is seated against the corresponding primary wall 246, and when each applicating element 224 is in its second position, the applicator pad is moved away from the respective primary wall 246 for placing the respective one of the pair of nasal appliques 10 on the nose 16 of the user.

With the basic structure of the nasal applique 10 and the corresponding applicator 200 described above, the following discussion focuses on an exemplary use of the nasal applique 10 and applicator 200. The applicator 200 is prepared for use by adjusting the position of the nose rest 204 relative to the base 202. In particular, the adjuster 212 (e.g., screw) may be rotated in the first or second rotational directions to selectively position the nose rest 204 relative to the base 202 so as to accommodate the size of the user's nose 16. A pair of nasal appliques 10 are then engaged with the applicator pads 234 via magnetic attraction between the metallic element 14 in the applique 10 and the magnet 14 coupled to the corresponding applicator pad 234. The applicator pad 234 and the defined by the stop member 226 may be generally complimentary in shape to the applique 10, so as to allow the applique 10 and applicator pad 234 to reside within the cavity when the applicating element is in the first position. The appliques 10 are coupled to the applicator pads 234 such that the adhesive portion of the applique 10 faces away from the applicator pad 234. The user may remove a peel-away layer from the applique 10 to expose the adhesive portion thereof.

With both appliques 10 coupled to the respective applicator pads 234, the user then positions his nose 16 adjacent the nose rest 204 and between the applicating elements 224. The user then presses on the arms 228 to flex the arms 228 toward each other, which causes the applicator pads 234 to become unseated from the primary wall 246 of the stop members 226. The user continues to press the arms 228 toward each other, until the flexible body 12 of the applique 10 engages with the user's nose 16 and is firmly pressed thereagainst. When the applique 10 initially contacts the user's nose 16, the applicator pad 234 may pivot relative to the arm 228 to conform to the particular anatomical profile of the nose 16. The user continues to apply pressure on the arms 228 to maintain secure engagement between the applique 10 and the user's skin while the adhesive takes hold between the user's skin and the flexible body 12.

After a period of time, the user may remove the applicator 200 from the user's nose 16 by sliding the applicator 200 down the user's nose toward the tip. As the user slides the applicator 200 away from the appliques 10, two opposing forces begin to interact with the applique 10. One force is an adhesive force holding the applique 10 on the user's nose, and a second force is a magnetic force between the magnet and the metallic element 14, which pulls the applique 10 toward the magnet, i.e., away from the nose 16. The adhesive on the applique 10 is strong enough to overcome the magnetic force, and thus, the applique 10 remains adhered to the nose 16 while the applicator 200 is slid off the user's nose 16.

The user may also release the pressure on the arms 228 to allow the arms 228 to transition from the second position toward the first position. As the user releases the pressure on the arms 228, the applicator pads 234 become seated against the primary wall 246 of the corresponding stop member 226, with the applicating elements 224 thereby assuming their respective first positions. In this respect, the arms 228 may be biased toward the first position, and thus, require force imparted by the user to cause the arms 228 to transition from the first position toward the second position.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. An applicator for placing a pair of nasal appliques on opposing lateral regions of a nose of a user, the applicator comprising:
   a base;
   a nose rest coupled to the base and adapted to rest adjacent the nose of the user;
   a pair of stop members coupled to the base and arranged in generally opposed relation to each other; and
   a pair of placement members coupled to the base, each placement member including an arm coupled to the base and a pad coupled to the arm, each placement member being engageable with a respective one of the pair of nasal appliques, each placement member being selectively transitional between a first position and a second position, when each placement member is in its first position, the placement member is positioned adjacent the respective one of the pair of stop members and when each placement member is in its second position, the placement member is moved away from the respective one of the pair of stop members for placing the respective one of the pair of nasal appliques on the nose of the user.

2. The applicator recited in claim 1, wherein the nose rest is translatably coupled to the base.

3. The applicator recited in claim 1, further comprising an adjuster coupled to the base and the nose rest, the adjuster enabling selective translational adjustment of the nose rest relative to the base.

4. The applicator recited in claim 1, wherein each placement member includes a magnet adapted to impart a magnetic force on a corresponding metallic element included in the respective one of the pair of nasal appliques.

5. The applicator recited in claim 1, wherein the pad is pivotally coupled to the arm.

6. The applicator recited in claim 1, wherein the arm and base allow the arm to flex relative to the base as the placement member transitions between the first and second positions.

7. The applicator recited in claim 1, wherein the arm is integrally coupled with the base.

8. The applicator recited in claim 1, wherein each stop member includes a primary wall and a peripheral wall extending from the primary wall, the primary wall and peripheral wall collectively defining a cavity adapted to receive at least a portion of a respective one of the pair of placement members in the first position.

9. The applicator recited in claim 8, wherein the primary wall is disposed about an opening through which the respective one of the pair of placement members extends.

10. An applicator for placing a pair of nasal appliques on opposing lateral regions of a nose of a user, the applicator comprising:
    a base;
    a nose rest translatably coupled to the base and adapted to rest adjacent the nose of the user;
    a pair of stop members coupled to the base and arranged in generally opposed relation to each other; and
    a pair of placement members coupled to the base, each placement member being engageable with a respective one of the pair of nasal appliques, each placement member being selectively transitional between a first position and a second position, when each placement member is in its first position, the placement member is positioned adjacent the respective one of the pair of stop members and when each placement member is in its second position, the placement member is moved away from the respective one of the pair of stop members for placing the respective one of the pair of nasal appliques on the nose of the user.

11. The applicator recited in claim 10, further comprising an adjuster coupled to the base and the nose rest, the adjuster enabling selective translational adjustment of the nose rest relative to the base.

12. The applicator recited in claim 10, wherein each placement member includes a magnet adapted to impart a magnetic force on a corresponding metallic element included in the respective one of the pair of nasal appliques.

13. The applicator recited in claim 10, wherein each stop member includes a primary wall and a peripheral wall extending from the primary wall, the primary wall and peripheral wall collectively defining a cavity adapted to receive at least a portion of a respective one of the pair of placement members in the first position.

14. The applicator recited in claim 13, wherein the primary wall is disposed about an opening through which the respective one of the pair of placement members extends.

15. An applicator for placing a pair of nasal appliques on opposing lateral regions of a nose of a user, the applicator comprising:
    a base;
    a nose rest coupled to the base and adapted to rest adjacent the nose of the user;
    a pair of stop members coupled to the base and arranged in generally opposed relation to each other; and
    a pair of placement members coupled to the base, each placement member being engageable with a respective one of the pair of nasal appliques, each placement member being selectively transitional between a first position and a second position, when each placement member is in its first position, the placement member is positioned adjacent the respective one of the pair of stop members and when each placement member is in its second position, the placement member is moved away from the respective one of the pair of stop members for placing the respective one of the pair of nasal appliques on the nose of the user;

wherein each stop member includes a primary wall and a peripheral wall extending from the primary wall, the primary wall and peripheral wall collectively defining a cavity adapted to receive at least a portion of a respective one of the pair of placement members in the first position.

16. The applicator recited in claim 15, further comprising an adjuster coupled to the base and the nose rest, the adjuster enabling selective translational adjustment of the nose rest relative to the base.

17. The applicator recited in claim 15, wherein each placement member includes a magnet adapted to impart a magnetic force on a corresponding metallic element included in the respective one of the pair of nasal appliques.

18. The applicator recited in claim 15, further comprising an adjuster coupled to the base and the nose rest, the adjuster enabling selective translational adjustment of the nose rest relative to the base.

19. The applicator recited in claim 15, wherein each placement member includes a magnet adapted to impart a magnetic force on a corresponding metallic element included in the respective one of the pair of nasal appliques.

* * * * *